United States Patent [19]

Sincock

[11] Patent Number: 5,129,886
[45] Date of Patent: Jul. 14, 1992

[54] REMOVAL AND SAFE DISPOSAL OF SHARPS FROM MEDICAL TOOLS

[75] Inventor: Brian F. Sincock, 26 Nioka Road, Dernancourt, S.A., Australia, 5075

[73] Assignees: Brian F. Sincock, Dernancourt; Ausmedics Pty. Ltd., Port Lincoln, both of Australia

[21] Appl. No.: 545,587

[22] Filed: Jun. 29, 1990

Related U.S. Application Data

[62] Division of Ser. No. 265,707, Nov. 1, 1988, Pat. No. 4,973,315.

[30] Foreign Application Priority Data

Nov. 11, 1987 [AU] Australia ................. PI5348

[51] Int. Cl.⁵ .............................................. A61M 5/32
[52] U.S. Cl. ................................. 604/192; 604/263; 206/365

[58] Field of Search ............... 604/192, 263, 187; 206/365, 366

[56] References Cited

U.S. PATENT DOCUMENTS

| | | | |
|---|---|---|---|
| 2,557,420 | 6/1951 | Elliott | 604/192 X |
| 4,485,918 | 12/1984 | Mayer | 604/192 X |
| 4,629,453 | 12/1986 | Cooper | 604/192 |

FOREIGN PATENT DOCUMENTS 2222370  3/1990  United Kingdom ................ 604/263

Primary Examiner—John D. Yasko
Attorney, Agent, or Firm—Fish & Richardson

[57] ABSTRACT

A sheath for the disposal of medical needles, the sheath having a tubular portion which is closed at one end. The other end is open and has gripping means to grip the boss portion of the needle. The sheath is then manipulated to remove the needle from the syringe, leaving the needle fully protected in the sheath.

6 Claims, 4 Drawing Sheets

REMOVAL AND SAFE DISPOSAL OF SHARPS FROM MEDICAL TOOLS

This application is a division of Ser. No. 07/265,707, filed Nov. 1, 1988, now U.S. Pat. No. 4,973,315.

BACKGROUND OF THE INVENTION

U.S. Pat. No. 4,592,744 to Jagger et al, describes a self re-sheathing safety case for a needle but this requires a special construction of syringe and even with its relative complexity is not entirely fool-proof.

U.S. Pat. No. 4,576,281 describes a needle disposal system in which needles are safely removed and dropped into a container but the point of the needle is still exposed in the container and as indicated can and often does penetrate the walls of the container and cause problems to disposal personnel.

This invention relates to improvements in the removal of sharp pointed sections of medical instruments and their safe disposal or the disposal of sharp pointed medical instruments or sharps as they are known.

Sharps may include needles for hypodermic syringes, canulas, scalpels, catheters or any other sharp pointed instruments used in medical treatment and which are generally of the disposable kind but which, because they have been used for treating ill people may be carrying disease organisms or other infectious bodies.

To meet stringent health and safety regulations and to minimize transmission of bacteria, viruses, disease or other organisms or other organisms having the potential to create disease or illness it is now a practice to dispose of the sharp or needle section of a medical device or the complete medical tool with the sharp or needle section attached once the medical tool has been used after coming into contact only once with a human body. In most cases, such as blood sample collection, it is necessary to remove the needle or other device from the medical tool and it is during this process that many occurrences of injury occur. Such injuries are referred to as needle stick injuries and it is to the prevention of needle stick injuries that this present invention is directed.

A further problem is that the procedure for the disposal of the sharps or needles at present whether or not they have been removed from a syringe is to drop them into a storage container which may then be destroyed by burning or the like. It is found, however, that needles may tend to puncture and project out of the sides of a container into which they have been placed and cause problems for disposal personnel as well. Hence, this invention is directed to preventing needles from being able to create further injury once they have been dropped into a disposal container.

It is one object of this invention therefore, to alleviate the necessity to handle a needle or the boss of a needle during the disposal process and to prevent that needle from being able to cause any further injury once removed.

U.S. Pat. No. 4,592,744 to Jagger et al. describes a self re-sheathing safety case for a needle but this requires a special construction of syringe and even with its relative complexity is not entirely fool-proof.

U.S. Pat. No. 4,576,281 describes a needle disposal system in which needles are safely removed and dropped into a container but the point of the needle is still exposed in the container and as indicated can and often does penetrate the walls of the container and cause problems to disposal personnel.

SUMMARY OF THE INVENTION

It is to overcoming these various problems that this present invention is directed.

In one form therefore, the invention is said to reside in a sheath for the disposal of medical sharps, the sheath comprising a tubular portion closed at one end and being open at the other, the open end of the sheath having a radially outwardly extending flange, the flange including means to guide the tip of a medical sharp into the tube and the inner surface of the tube in the region of the flange including means to grippingly engage a boss portion of the medical sharp.

This sheath therefore is long enough to completely encase the needle or sharp and then holds it rigid so that the needle or sharp cannot project out of the sides of the sheath or the bottom of the sheath. The flange is of a sufficient size to enable the sheath to be held in the hand while directing the point of the medical sharp into the tube with the fingers being protected. Once the boss of the medical sharp is received and held in the gripping portion of the tube the syringe or other device can be rotated to release the sharp from the medical tool and then one or either parts can be disposed of. Alternatively, the medical tool and the sharp attached may be disposed of as a single unit with complete safety.

Preferably the outer surface of the tube adjacent to the flange includes ribs to assist with grasping of the sheath for the removal process.

The means to grippingly engage the boss of a medical sharp may include a plurality of longitudinal ridges extending radially inwards from the inner surface of the tube to enable gripping of the boss by the ridges.

Alternatively, the means to grippingly engage the boss of the medical sharp may include an inside portion of the tube being substantially cylindrical and having a diameter to engage with an interference fit the boss of the medical sharp.

The means to guide the tip of the medical sharp into the tube may comprise a bevelled surface between the flange and the inner surface of the tube.

In another form, the invention may reside in a medical sharp disposal rack comprising a tray having an upper substantially planar horizontal surface with a plurality of apertures thereon and apertures receiving and supporting a plurality of sheaths as defined above with their open ends upward.

By this means the sheaths may be supported during the removal stage so that the user's second hand may be kept completely away from the tip of the medical sharp thereby completely eliminating any danger. Once the boss of the medical sharp has been firmly engaged in the gripping portion of the tube then the sheath while still connected to the medical tool may be removed from the tray and either disposed of as discussed above as a complete unit or the sheath with the sharp engaged therein can be removed from the medical tool and disposed of separately.

Alternatively, the invention may be said to reside in a medical sharp disposal tray having an upper substantially planar and horizontal surface with a plurality of tubes extending from apertures in the surface and having closed lower ends, each tube having a bevelled portion between the planar surface and the inner surface of the tube to assist with guiding the tip of a medical sharp into the tube and having means to grippingly engage the boss at the base of a medical sharp when inserted into the tube.

By this form of the invention the medical sharps may be received in the tubes in the disposal tray and then when all of the tubes in the tray are full the entire lot may be disposed of.

It will be realized that where medical sharps have different arrangements of bosses or gripping means at the base of their pointed section then other gripping means are within the scope of this invention to enable the pointed section to be clearly protected as described above.

It will be noted that with the various forms of the invention as discussed above it is not necessary for a user to remove the needle section manually from the medical tool before it is inserted into the sheath and thereby there is much less chance of injury from the medical sharp.

It may not be necessary for the user to remove the needle section from the medical tool prior to disposal and in this situation a firm downward movement of the sheath onto a hard surface, once it is installed onto the medical sharp will more tightly affix the sheath to the needle section of the medical tool and the needle section to the medical tool itself so that the medical tool and sharp and sheath can be disposed of as a single unit. This again provides considerable safety because the needle cannot enter the user.

If desired, there may be further provided within each tube of either the sheath or the fixed construction as discussed above, a foam or other compound to assist with holding a needle where perhaps such needles do not have a boss which will be easily engaged into the sheath.

In general, therefore, this invention provides a safe method for the removal of medical sharps from a medical tool and their disposal and hence in a further embodiment the invention is said to reside in a method of safe removal of medical sharps from medical tools and the disposal of medical sharps substantially as earlier discussed. It will be particularly noted that the method requires only a one handed operation and hence as one hand is holding the medical tool the other hand can be placed well away so that there is no danger of a needle piercing the skin of a user and perhaps transmitting a disease such as AIDS.

This then generally describes the invention but to more clearly assist with understanding the invention reference will now be made to the accompanying drawings which shows preferred embodiments of the invention and show how the invention is used.

DESCRIPTION OF THE PREFERRED EMBODIMENTS

Figure 1:
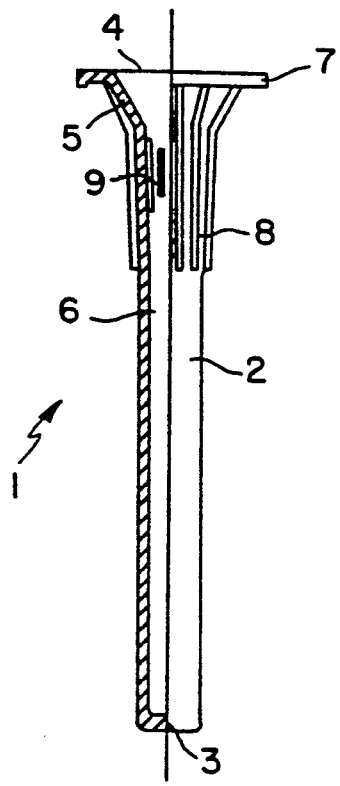
FIG. 1 shows in part cross-section a sheath for the removal and disposal of medical sharps.

Now looking more closely at the drawings and in particular FIG. 1 it will be seen that the sheath generally shown as 1 comprises a tubular portion 2 having a closed end 3 and an open end 4. The open end has a bevelled inner surface 5 to assist with guiding the tip of a medical sharp into the hollow part 6 of the tube 2. A flange 7 extends radially outwardly from the open end 4 of the sheath 1 and the size of the flange is such that if the sheath is held by the fingers then the fingers will be substantially guarded by the flange. On the outside of the sheath 1 are a number of ridges or ribs 8 underneath the flange 7 so that the outside of the sheath may be grasped while the needle is being removed once the boss has been engaged in the tube. To assist with engaging the boss into the tube the inner surface of the tube 2 immediately adjacent the open end includes longitudinal ridges 9 which engage the boss of a medical sharp to assist with removal.

Figure 2:
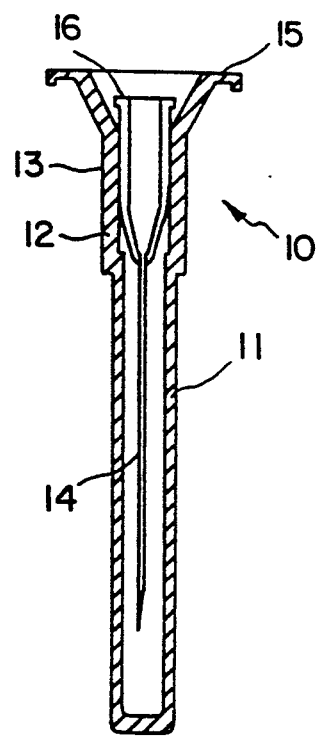
FIG. 2 shows a cross-sectional view of an alternative sheath for the removal of medical sharps with a hypodermic syringe needle in the sheath.

An alternative embodiment of medical sharp removal sheath is shown in FIG. 2 with a hypodermic syringe needle engaged therein. In this embodiment the gripping region 10 of the tube 11 includes a substantially cylindrical inner surface 12 to engage with an interference fit around the boss 13 of a medical sharp. It will be seen that the needle 14 of the medical sharp is well protected in the sheath and cannot move sideways and pierce the walls of the tubular portion of the sheath.

It will be also noted that the top 16 of the boss is recessed well below the flange area 15 and hence the medical sharp cannot easily be removed for illegal further use.

Figure 3:
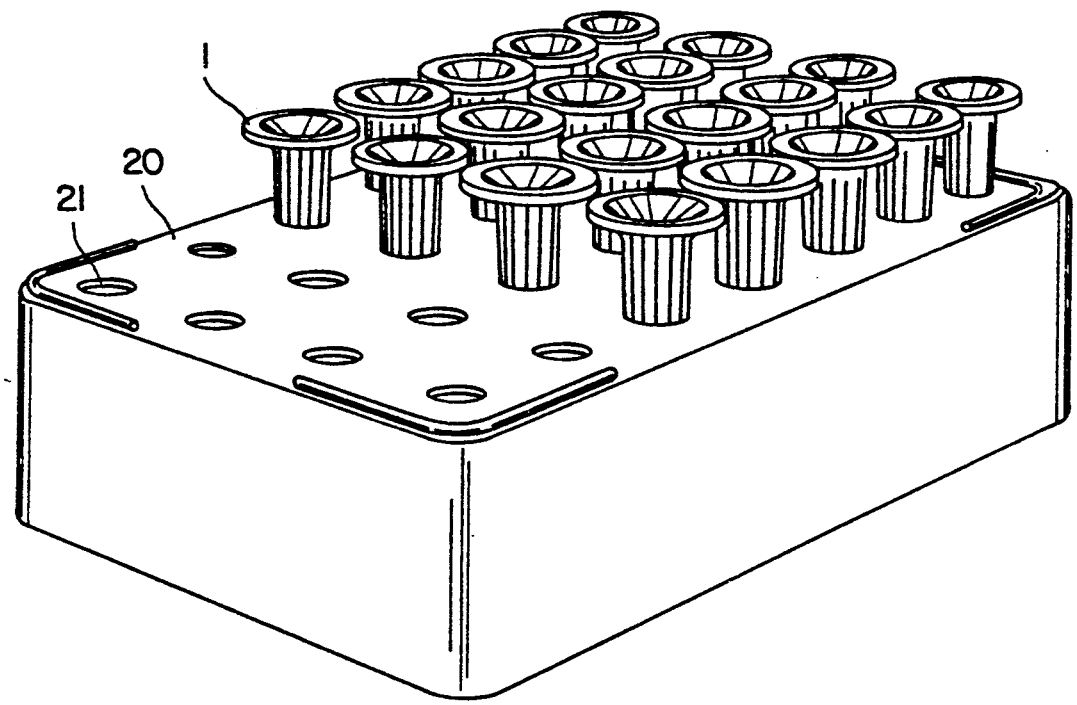
FIG. 3 shows a disposal tray with a number of sheaths supported therein.

FIG. 3 shows a number of sheaths 1 engaged in a tray 20. The tray includes a number of apertures 21 into which the sheaths 1 are received. The sheaths are supported in the tray by the ends of the ribs 8 on edges of the apertures 21, but can easily be removed as they are loosely held.

Figure 4:
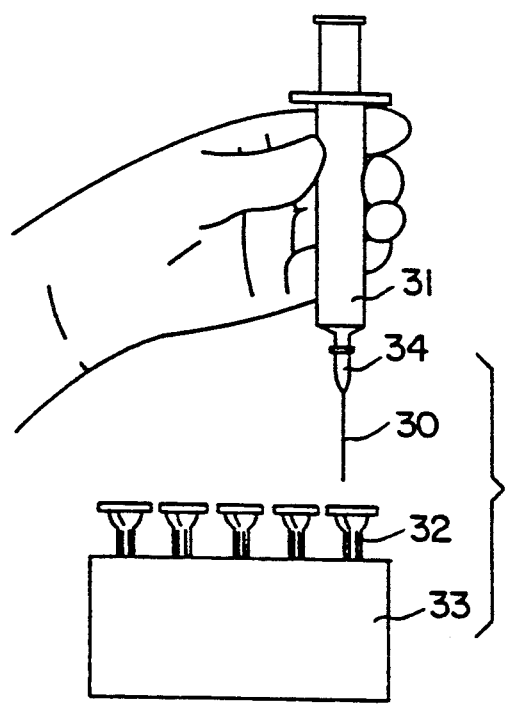
FIGS. 4 to 8 show the various stages in the process of removal of a medical sharp from a hypodermic syringe and FIG. 9 shows an alternative embodiment of medical sharp disposal tray.

Now looking at FIGS. 4 to 8 which show the various stages in the removal of a needle it will be seen in FIG. 4 that a syringe is being held in one hand with the point 30 of the syringe 31 pointed down into one of the sheaths 32 supported in the tray 33. It will be noted that only one hand is necessary to hold the syringe and the other hand is completely away from the tray 33.

Figure 5:
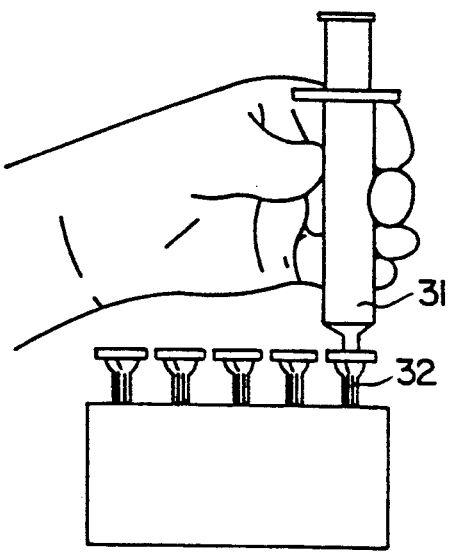
Figure 6:
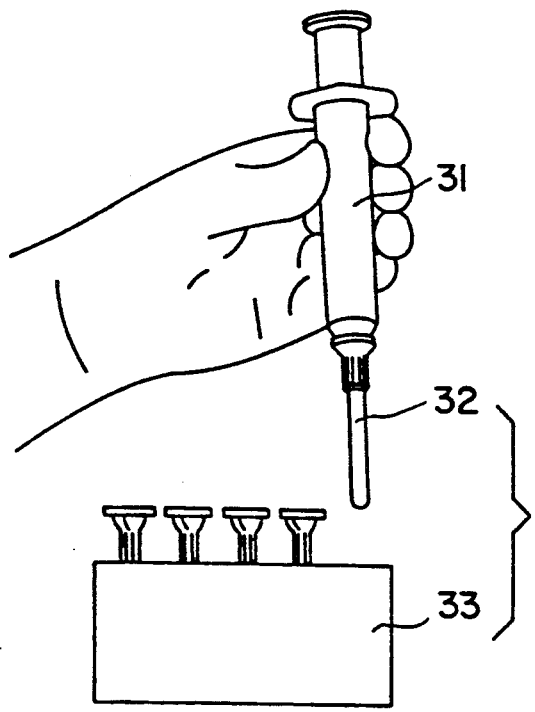
Figure 7:
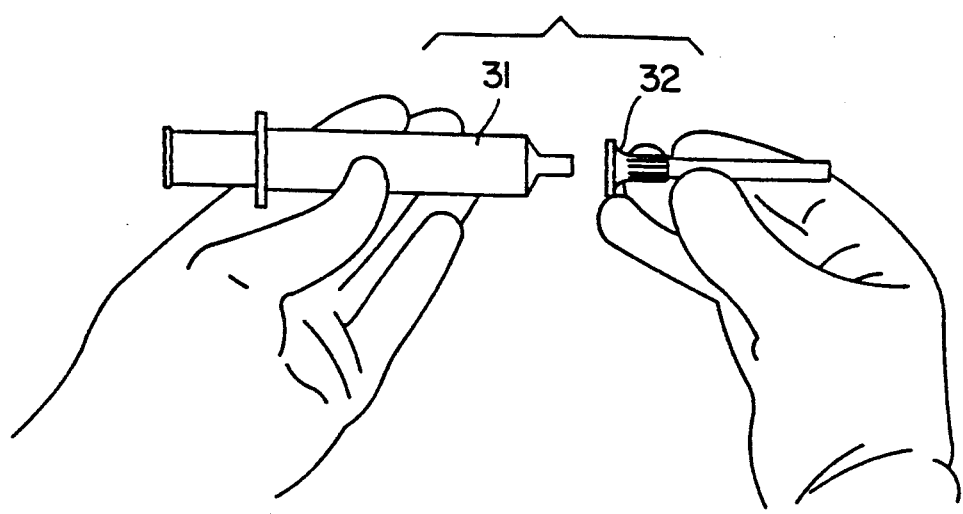

The needle 30 is pushed into the tube of the sheath 32 until the boss 34 as shown in FIG. 4 is completely pushed into the tube as can be seen in FIG. 5. As can be seen in FIG. 6 the sheath 32 is then engaged onto the syringe 31 and the sheath is removed from the tray 33 and then as shown in FIG. 7 both hands can be used to remove the sheath 32 from the tool 31 leaving the needle fully protected by the sheath.

Figure 8:
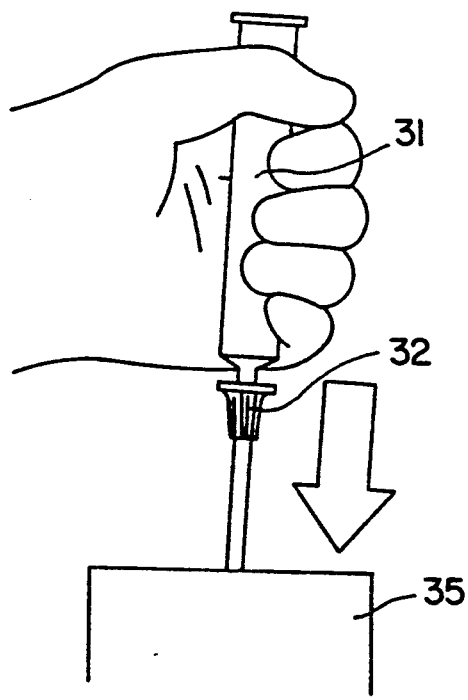

Alternatively, as shown in FIG. 8 from the stage shown in FIG. 6 the medical tool 31 with the sheath 32 engaged can be struck onto a hard surface 35 thereby firmly engaging the boss of the needle into the sheath and the syringe firmly into the boss so that the two portions can be disposed of together.

Figure 9:
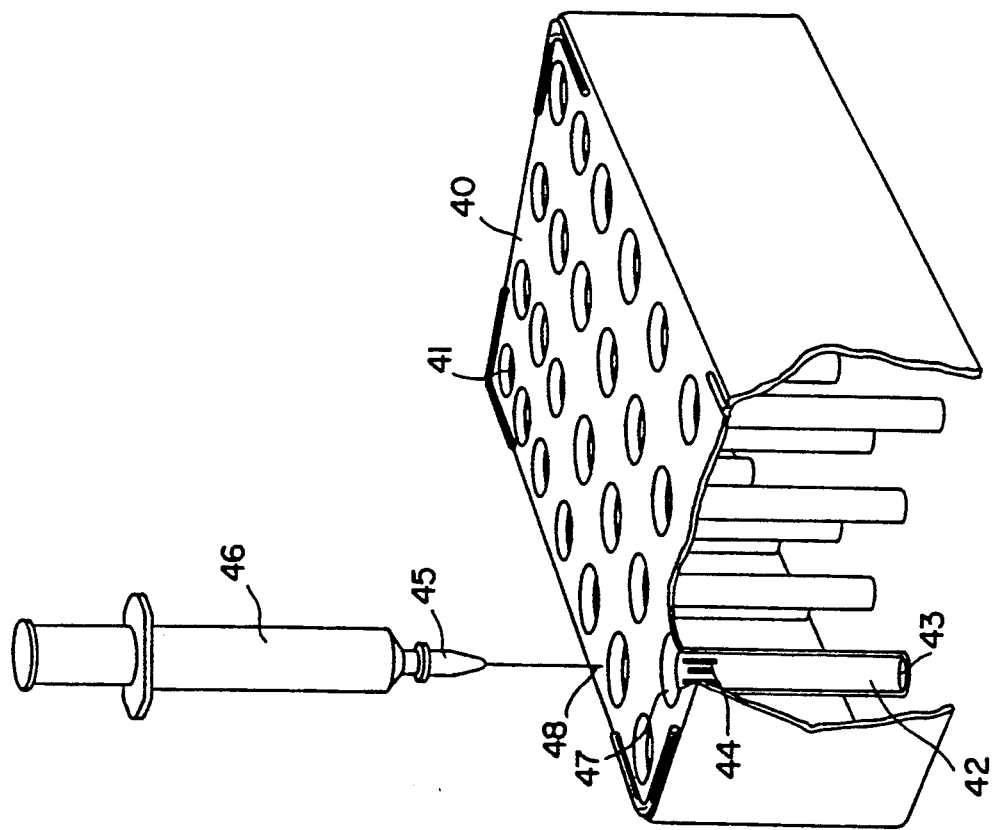

FIG. 9 shows an alternative embodiment where a tray 40 includes a number of apertures 41. Each aperture includes a tubular portion 42 closed at its lower end 43 and including gripping ribs 44 to engage the boss 45 of a syringe 46. There is a bevelled portion 47 between the planar upper surface of the tray 40 and the tube 42 to assist with guiding the point 48 of a needle into the tube. Once the boss 45 has been firmly engaged in the tube 42 then the syringe 46 may be twisted to remove the needle therefrom and to leave the needle firmly engaged in the tray 40. Once all of the apertures in the tray have been filled the tray as a whole may then be disposed of.

The materials of construction of the sheath and tray or moulded sheath and tray combination may be any plastics material such as polyethylene or polypropylene or alternatively the tray may be made from cardboard or other suitable material. The preferred method of construction is by injection-moulding but other methods may also be used.

I claim:

1. An apparatus for receiving and holding medical sharps for disposal, comprising:
   a planar surface containing a plurality of apertures therein;
   a plurality of sheaths for receipt and disposal of said sharps, each of said sheaths attached to and formed as one piece with said planar surface and extending perpendicularly from one of said apertures, each of said sheaths comprising a tubular portion closed at a lower end and open at an upper end, the upper inner surface of said sheaths comprising means for grippingly engaging a boss portion of said medical sharp.

2. The apparatus of claim 1, wherein said planar surface is substantially horizontal and said sheaths extend downward from said apertures.

3. The apparatus of claim 1, wherein said means for grippingly engaging a boss portion of a medical sharp comprises a plurality of ridges extending radially inward from the inner surface of the tubular portion.

4. The apparatus of claim 1, wherein said means for grippingly engaging a boss portion of a medical sharp comprises an inside portion of the tubular portion which is substantially cylindrical and has an inside diameter chosen so as to engage the boss portion with an interference fit.

5. The apparatus of claim 1, wherein the open upper end of each of said sheaths comprises means for assisting in guiding a tip of a medical sharp into the sheath.

6. The apparatus of claim 5, wherein said means for assisting in guiding a tip of a medical sharp into the sheath comprises a bevelled surface at the upper open end of the sheath.

* * * * *